United States Patent
Schilling et al.

(10) Patent No.: US 11,452,860 B2
(45) Date of Patent: Sep. 27, 2022

(54) POWER SOURCE SELECTION FOR A FULLY IMPLANTABLE LVAD SYSTEM

(71) Applicant: Medtronic, Inc., Minneapolis, MN (US)

(72) Inventors: Eric A. Schilling, Ham Lake, MN (US); Jacob A. Roe, North St Paul, MN (US); Joel B. Artmann, Elk River, MN (US); Jason C. Lee, Edina, MN (US); Jonathan P. Roberts, Coon Rapids, MN (US); David J. Peichel, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 5 days.

(21) Appl. No.: 16/944,564

(22) Filed: Jul. 31, 2020

(65) Prior Publication Data
US 2022/0031919 A1 Feb. 3, 2022

(51) Int. Cl.
| A61M 1/12 | (2006.01) |
| A61M 60/50 | (2021.01) |
| A61M 60/148 | (2021.01) |
| A61M 60/871 | (2021.01) |

(52) U.S. Cl.
CPC .......... *A61M 60/50* (2021.01); *A61M 60/148* (2021.01); *A61M 60/871* (2021.01); *A61M 2205/3365* (2013.01); *A61M 2205/52* (2013.01); *A61M 2205/8206* (2013.01)

(58) Field of Classification Search
CPC ........ A61M 60/122; A61M 2205/8206; A61M 60/871; A61M 2205/3507; A61M 2205/8243; A61M 60/00; A61M 60/50
See application file for complete search history.

(56) References Cited

U.S. PATENT DOCUMENTS

| 7,505,816 | B2 | 3/2009 | Schmeling et al. |
| 7,997,854 | B2 | 8/2011 | LaRose et al. |
| 8,419,609 | B2 | 4/2013 | Shambaugh, Jr. et al. |
| 10,143,788 | B2 | 12/2018 | Rudser et al. |
| 10,376,624 | B2 | 8/2019 | Rudser et al. |
| 10,500,324 | B2 | 12/2019 | Schade et al. |
| 10,525,181 | B2 | 1/2020 | Petersen |
| 2007/0142696 | A1* | 6/2007 | Crosby ................ A61M 60/00 600/16 |
| 2009/0157148 | A1 | 6/2009 | Phillips et al. |
| 2009/0251101 | A1 | 10/2009 | Phillips et al. |
| 2010/0063347 | A1 | 3/2010 | Yomtov et al. |
| 2015/0290375 | A1 | 10/2015 | Angwin et al. |
| 2015/0290379 | A1 | 10/2015 | Rudser et al. |
| 2017/0326283 | A1 | 11/2017 | Schade et al. |

(Continued)

OTHER PUBLICATIONS

International Search Report and Written Opinion of International Application No. PCT/US2021/041745, dated Oct. 7, 2021, 12 pp.

*Primary Examiner* — Jon Eric C Morales
(74) *Attorney, Agent, or Firm* — Shumaker & Sieffert, P.A.

(57) ABSTRACT

A method of managing multiple power sources for an implantable blood pump includes operating the implantable blood pump with both power from an internal battery, the internal battery being disposed within an implantable controller and in communication with the implantable blood pump, and with transcutaneous energy transfer system (TETS) power in communication with the implantable blood pump, if TETS power is available.

20 Claims, 3 Drawing Sheets

(56) References Cited

U.S. PATENT DOCUMENTS

2018/0280708 A1 10/2018 Escalona et al.
2019/0076587 A1 3/2019 Rudser et al.
2019/0314564 A1 10/2019 Rudser et al.
2019/0365972 A1 12/2019 Roelle et al.

* cited by examiner

POWER SOURCE SELECTION FOR A FULLY IMPLANTABLE LVAD SYSTEM

CROSS-REFERENCE TO RELATED APPLICATION n/a.

FIELD

The present technology is generally related to power source selection methods and systems for an implantable blood pump.

BACKGROUND

Fully implantable blood pumps include an implanted controller having an internal battery that provides power to the blood pump along with the capability to receive power from a transcutaneous energy transfer system (TETS). With multiple modalities from which to power the pump comes a need to identify which power source should provide power the pump.

SUMMARY

The techniques of this disclosure generally relate to power source selection methods and system for an implantable blood pump.

In one aspect, a method of managing multiple power sources for an implantable blood pump includes operating the implantable blood pump with both power from an internal battery, the internal battery being disposed within an implantable controller and in communication with the implantable blood pump, and with transcutaneous energy transfer system (TETS) power in communication with the implantable blood pump, if TETS power is available.

In another aspect of this embodiment, the method further includes operating the implantable blood pump with only TETS power if: a set speed of the implantable blood pump is able to be maintained by TETS power alone and an internal battery capacity is greater than a predetermined reserve threshold.

In another aspect of this embodiment, the method further includes operating the implantable blood pump with only TETS power if: a minimum speed of the implantable blood pump is able to be maintained by TETS power alone and an internal battery capacity is less than a predetermined reserve threshold.

In another aspect of this embodiment, the method further includes operating the implantable blood pump with only TETS power if power from the internal battery is unavailable.

In another aspect of this embodiment, the method further includes operating the implantable blood pump only with power from the internal battery if TETS power is unavailable.

In another aspect of this embodiment, the method further includes operating the implantable blood pump only with power from the internal battery if the battery learning cycle is required and all the prerequisites for a battery learning cycle are met.

In one aspect, a method of managing multiple power sources for an implantable blood pump includes operating the implantable blood pump with both power from an internal battery, the internal battery being disposed within an implantable controller and in communication with the implantable blood pump, and with transcutaneous energy transfer system (TETS) power in communication with the implantable blood pump, if during operation of the implantable blood pump: a minimum speed of the implantable blood pump is unable to be maintained by TETS power alone and an internal battery capacity is less than a predetermined reserve threshold or a set speed of the implantable blood pump is unable to be maintained by TETS power alone and an internal battery capacity is greater than a predetermined reserve threshold.

In another aspect of this embodiment, the method further includes operating the implantable blood pump with only TETS power if power from the internal battery is unavailable.

In another aspect of this embodiment, the method further includes operating the implantable blood pump only with power from the internal battery if TETS power is unavailable.

In another aspect of this embodiment, the method further includes operating the implantable blood pump only with power from the internal battery if the battery learning cycle is required and all the prerequisites for a battery learning cycle are met.

In one aspect, a control circuit for an implantable blood pump includes processing circuitry configured to operate the implantable blood pump with both power from an internal battery, the internal battery being disposed within an implantable controller and in communication with the implantable blood pump, and with transcutaneous energy transfer system (TETS) power in communication with the implantable blood pump, if TETS power is available and if battery operation is not required.

In another aspect of this embodiment, the processing circuitry is further configured to operate the implantable blood pump with only TETS power if: a set speed of the implantable blood pump is able to be maintained by TETS power alone and an internal battery capacity is greater than a predetermined reserve threshold.

In another aspect of this embodiment, the processing circuitry is further configured to operate the implantable blood pump with only TETS power if: a minimum speed of the implantable blood pump is able to be maintained by TETS power alone and an internal battery capacity is less than a predetermined reserve threshold.

In another aspect of this embodiment, the processing circuitry is further configured to operate the implantable blood pump with only TETS power if power from the internal battery is unavailable.

In another aspect of this embodiment, the processing circuitry is further configured to operate the implantable blood pump only with power from the internal battery if TETS power is unavailable.

In another aspect of this embodiment, the processing circuitry is further configured to operate the implantable blood pump only with power from the internal battery if the battery learning cycle is required and all the prerequisites for the battery learning cycle are met.

In one aspect, a control circuit for an implantable blood pump includes processing circuitry configured to: operate the implantable blood pump with both power from an internal battery, the internal battery being disposed within an implantable controller and in communication with the implantable blood pump, and with transcutaneous energy transfer system (TETS) power in communication with the implantable blood pump, if during operation of the implantable blood pump: a minimum speed of the implantable blood pump is unable to be maintained by TETS power alone and an internal battery capacity is less than a predetermined reserve threshold or a set speed of the implantable blood pump is unable to be maintained by TETS power alone and an internal battery capacity is greater than a predetermined reserve threshold.

In another aspect of this embodiment, the processing circuitry is further configured to operate the implantable blood pump with only TETS power if power from the internal battery is unavailable.

In another aspect of this embodiment, the processing circuitry is further configured to operate the implantable blood pump only with power from the internal battery if TETS power is unavailable.

In another aspect of this embodiment, the processing circuitry is further configured to operate the implantable blood pump only with power from the internal battery if the battery learning cycle is required and all the prerequisites for a battery learning cycle are met.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
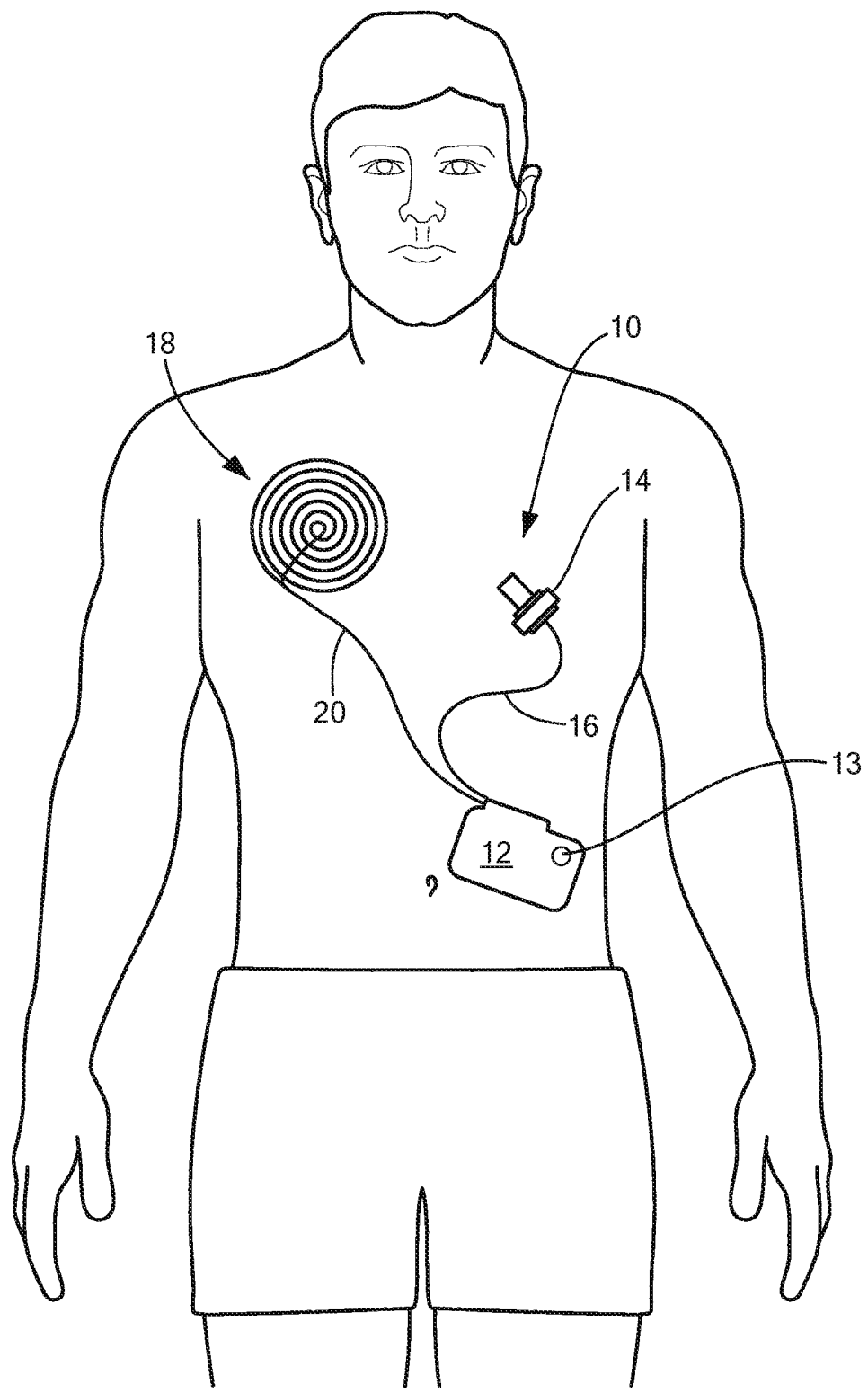
FIG. 1 is an internal system view of an implantable blood pump with a TETS receiver source constructed in accordance with the principles of the present application.
Figure 2:
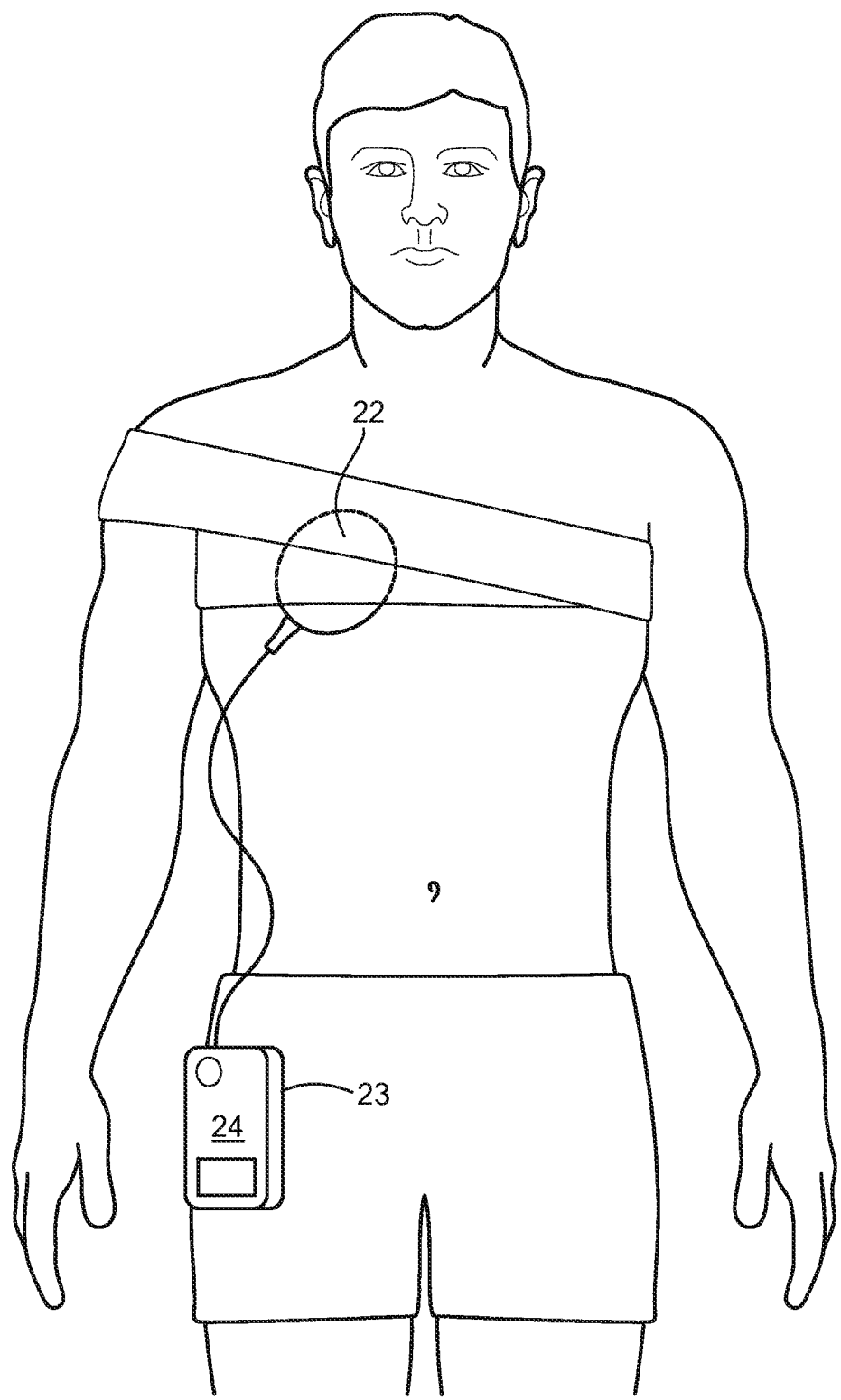
FIG. 2 is an external view of a TETS transmitter and a controller of the system shown in FIG. 1.

Referring now to the drawings in which like reference designators refer to like elements there is shown in FIGS. 1 and 2 an exemplary mechanical circulatory support device ("MCSD") constructed in accordance with the principles of the present application and designated generally as "10." The MCSD 10 may be fully implantable within a patient, whether human or animal, which is to say there are no percutaneous connections between the implanted components of the MCSD 10 and the components outside of the body of the patient. In the configuration shown in FIG. 1, the MCSD 10 includes an internal controller 12 implanted within the body of the patient. The internal controller 12 includes a control circuit having processing circuitry configured to control operation of an implantable blood pump 14. The internal controller 12 may include an internal power source 13, configured to power the components of the controller and provide power to one or more implantable medical devices, for example, the implantable blood pump, such as a ventricular assist device ("VAD") 14 implanted within the left ventricle of the patient's heart. The power source 13 may include a variety of different types of power sources including an implantable battery. VADs 14 may include centrifugal pumps, axial pumps, or other kinds electromagnetic pumps configured to pump blood from the heart to blood vessels to circulate around the body. One such centrifugal pump is the HVAD and is shown and described in U.S. Pat. No. 7,997,854, the entirety of which is incorporated by reference. One such axial pump is the MVAD and is shown and described in U.S. Pat. No. 8,419,609, the entirety of which is incorporated herein by reference. In an exemplary configuration, the VAD 14 is electrically coupled to the internal controller 12 by one or more implanted conductors 16 configured to provide power to the VAD 14, relay one or more measured feedback signals from the VAD 14, and/or provide operating instructions to the VAD 14.

Continuing to refer to FIG. 1, a receiving or internal coil 18 may also be coupled to the internal controller 12 by, for example, one or more implanted conductors 20. In an exemplary configuration, the receiving coil 18 may be implanted subcutaneously proximate the thoracic cavity, although any subcutaneous position may be utilized for implanting the receiving coil 18. The receiving coil 18 is configured to be inductively powered through the patient's skin by a transmission or external coil 22 (seen in FIG. 2) disposed opposite the receiving coil 18 on the outside/exterior of the patient's body. For example, as shown in FIG. 2, a transmission coil 22 may be coupled to an external controller 23 having a power source 24, for example, a portable battery carried by the patient or wall power. In one configuration, the battery is configured to generate a radiofrequency signal for transmission of energy from the transmission coil 22 to the receiving coil 18. The receiving coil 18 may be configured for transcutaneous inductive communication with the transmission coil 22 to define a transcutaneous energy transfer system (TETS) that receives power from the transmission coil.

Figure 3:
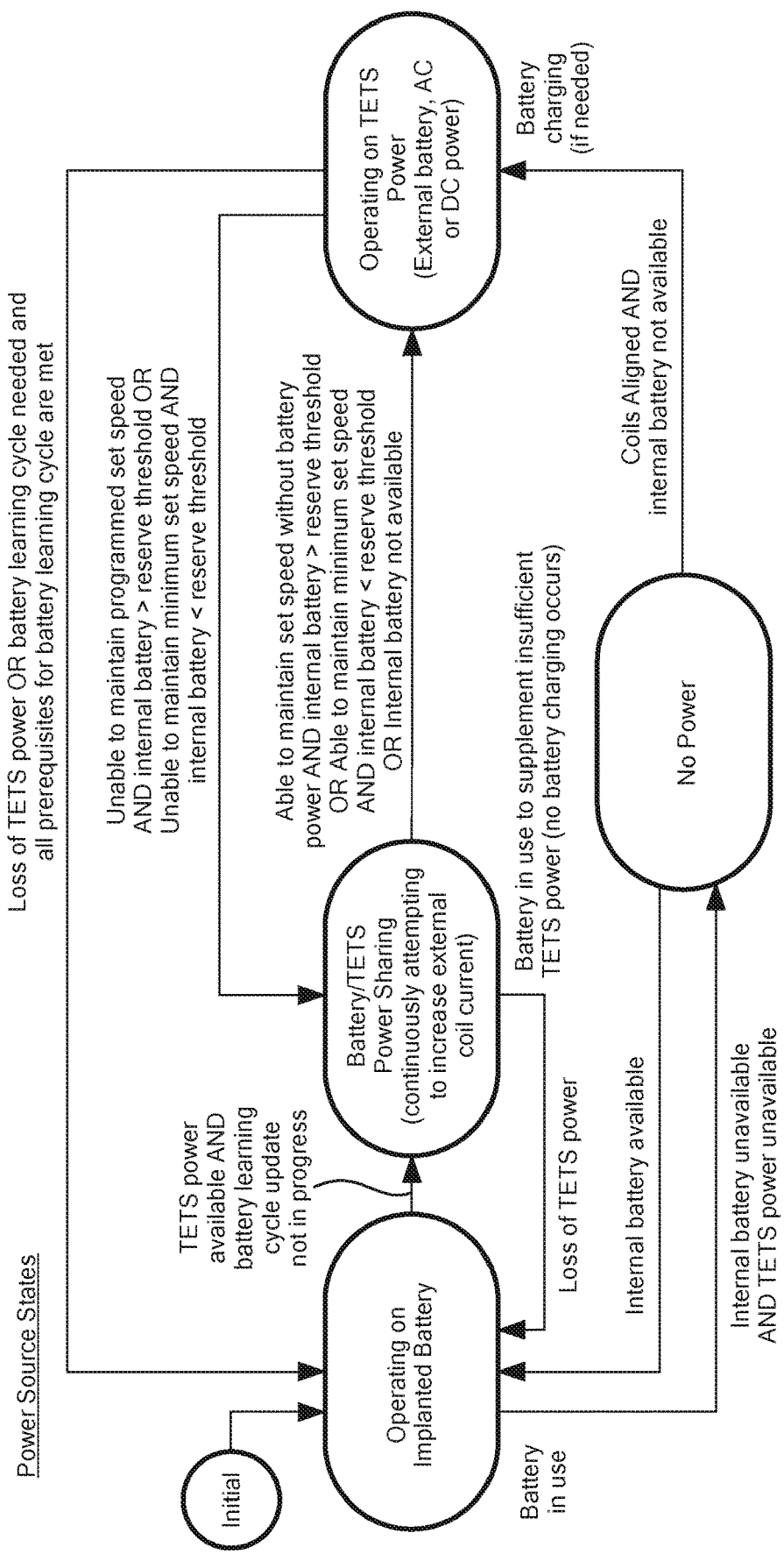
FIG. 3 is a flow chart showing how multiple power sources are utilized by the controller.

Referring now to FIG. 3, in which a method of managing multiple power sources for pump 14 is shown. Initially, the controller 12 operates the pump 14 with power from the internal power source 13 only. That is, when the pump 14 initially starts, if internal battery power is available the controller 12 instructs the pump to utilize internal battery power for operating. However, if TETS power is available and battery operation, such a s battery learning cycle, is not in progress, the pump 14 operates on shared power from both TETS power and power from the internal battery 13. In particular, when on shared power mode, the controller 12 continuously attempts to increase current to the exterior coil 22 to increase power available from TETS to power the pump 14. During power sharing mode, the internal battery is not charged by TETS power, but instead both TETS power and internal battery power are utilized to power the pump 14. In particular, TETS power and internal battery power are simultaneously utilized to power the pump 14. However, the controller 12 switches from operating on shared power to operating the pump 14 on TETS power if: the internal battery power is not available, which may be for example, when the battery is fully discharged or there is an error with the battery; a set speed of the implantable blood pump 14 is able to be maintained by TETS power alone and an internal battery power is greater than a predetermined reserve threshold; or minimum speed of the implantable blood pump 14 is able to be maintained by TETS power alone and an internal battery power is less than a predetermined reserve threshold.

The controller 12 is configured to switch back from TETS only mode to a shared power mode if a minimum speed of the implantable blood pump 14 is unable to be maintained by TETS power alone and an internal battery power is less than a predetermined reserve threshold or a set speed of the implantable blood pump 14 is unable to be maintained by TETS power. Moreover, the controller 12 switches from operating on TETS power to internal battery power only if TETS power is unavailable or a battery learning cycle is required and all the prerequisites for the battery learning cycle are met, which may include criterial such as internal battery capacity above a predetermined threshold or that no system or power faults are present. Situations where TETS power is unavailable may include but are not limited to when the coils 18 and 22 are not aligned, the patient removes the transmission coil 22, or if either of the coils 18 or 22 exceed a predetermined temperature threshold that the TETS turns off.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of managing multiple power sources for an implantable blood pump, comprising:
    operating the implantable blood pump with both power from an internal battery and transcutaneous energy transfer system (TETS) power simultaneously, the internal battery being disposed within an implantable controller and in communication with the implantable blood pump, and the TETS in communication with the implantable blood pump.

2. The method of claim 1, further including subsequently switching the implantable blood pump to operate with only TETS power if:
    a set speed of the implantable blood pump is able to be maintained by TETS power alone and an internal battery capacity is greater than a predetermined reserve threshold.

3. The method of claim 1, further including subsequently switching the implantable blood pump to operate with only TETS power if:
    a minimum speed of the implantable blood pump is able to be maintained by TETS power alone and an internal battery capacity is less than a predetermined reserve threshold.

4. The method of claim 1, further including subsequently switching the implantable blood pump to operate with only TETS power if power from the internal battery is unavailable.

5. The method of claim 1, further including subsequently switching the implantable blood pump to operate only with power from the internal battery if TETS power is unavailable.

6. The method of claim 1, further including subsequently switching the implantable blood pump to operate only with power from the internal battery if a battery learning cycle is required and all the prerequisites for the battery learning cycle are met.

7. A method of managing multiple power sources for an implantable blood pump, comprising:
    operating the implantable blood pump with both power from an internal battery and transcutaneous energy transfer system (TETS) power simultaneously, the internal battery being disposed within an implantable controller and in communication with the implantable blood pump, and the TETS in communication with the implantable blood pump, if during operation of the implantable blood pump:
        a minimum speed of the implantable blood pump is unable to be maintained by TETS power alone and an internal battery capacity is less than a predetermined reserve threshold; or
        a set speed of the implantable blood pump is unable to be maintained by TETS power alone and the internal battery capacity is greater than the predetermined reserve threshold.

8. The method of claim 7, further including subsequently switching the implantable blood pump to operate with only TETS power if power from the internal battery is unavailable.

9. The method of claim 7, further including subsequently switching the implantable blood pump to operate only with power from the internal battery if TETS power is unavailable.

10. The method of claim 7, further including subsequently switching the implantable blood pump to operate only with power from the internal battery if a battery learning cycle is required and all the prerequisites for the battery learning cycle are met.

11. A control circuit for an implantable blood pump, comprising:
    processing circuitry configured to:
        operate the implantable blood pump with both power from an internal battery and transcutaneous energy transfer system (TETS) power simultaneously, the internal battery being disposed within an implantable controller and in communication with the implantable blood pump, and the TETS in communication with the implantable blood pump, if TETS power is available and if battery only operation is not required.

12. The control circuit of claim 11, wherein the processing circuitry is further configured to subsequently switch the implantable blood pump to operate with only TETS power if:
   a set speed of the implantable blood pump is able to be maintained by TETS power alone and an internal battery capacity is greater than a predetermined reserve threshold.

13. The control circuit of claim 11, wherein the processing circuitry is further configured to subsequently switch the implantable blood pump to operate with only TETS power if:
   a minimum speed of the implantable blood pump is able to be maintained by TETS power alone and an internal battery capacity is less than a predetermined reserve threshold.

14. The control circuit of claim 11, wherein the processing circuitry is further configured to subsequently switch the implantable blood pump to operate only with TETS power if power from the internal battery is unavailable.

15. The control circuit of claim 11, wherein the processing circuitry is further configured to subsequently switch the implantable blood pump to operate only with power from the internal battery if TETS power is unavailable.

16. The control circuit of claim 11, wherein the processing circuitry is further configured to subsequently switch the implantable blood pump to operate only with power from the internal battery if a battery learning cycle is required and all the prerequisites for the battery learning cycle are met.

17. A control circuit for an implantable blood pump, comprising:
   processing circuitry configured to:
   operate the implantable blood pump with both power from an internal battery and transcutaneous energy transfer system (TETS) power simultaneously, the internal battery being disposed within an implantable controller and in communication with the implantable blood pump, and the TETS in communication with the implantable blood pump, if during operation of the implantable blood pump:
      a minimum speed of the implantable blood pump is unable to be maintained by TETS power alone and an internal battery capacity is less than a predetermined reserve threshold; or
      a set speed of the implantable blood pump is unable to be maintained by TETS power alone and the internal battery capacity is greater than the predetermined reserve threshold.

18. The control circuit of claim 17, wherein the processing circuitry is further configured to subsequently switch the implantable blood pump to operate with only TETS power if power from the internal battery is unavailable.

19. The control circuit of claim 17, wherein the processing circuitry is further configured to subsequently switch the implantable blood pump to operate only with power from the internal battery if TETS power is unavailable.

20. The control circuit of claim 17, wherein the processing circuitry is further configured to subsequently switch the implantable blood pump to operate only with power from the internal battery if a battery learning cycle is required and all the prerequisites for the battery learning cycle are met.

* * * * *